United States Patent
James et al.

(10) Patent No.: US 6,555,332 B2
(45) Date of Patent: Apr. 29, 2003

(54) FLUORESCENT DETECTION METHOD FOR MICROORGANISMS BASED ON NITROCOUMARINS

(75) Inventors: Arthur James, Newcastle-Upon-Tyne (GB); Daniel Monget, Saint Sorlin en Bugey (FR)

(73) Assignee: Biomerieux S.A., Marcy l'Etoile (FR)

( * ) Notice: Subject to any disclaimer, the term of this patent is extended or adjusted under 35 U.S.C. 154(b) by 0 days.

(21) Appl. No.: 09/848,250

(22) Filed: May 4, 2001

(65) Prior Publication Data

US 2002/0031795 A1 Mar. 14, 2002

Related U.S. Application Data

(63) Continuation of application No. PCT/FR99/02704, filed on Nov. 5, 1999.

(30) Foreign Application Priority Data

Nov. 5, 1998 (FR) .............................................. 98 14101

(51) Int. Cl.$^7$ ................................................. C12Q 1/04
(52) U.S. Cl. ............................ 435/34; 435/39; 514/457
(58) Field of Search ....................... 435/34, 39; 514/457

(56) References Cited

U.S. PATENT DOCUMENTS

| | | | | |
|---|---|---|---|---|
| 4,728,608 A | | 3/1988 | Roberts et al. ................ | 435/34 |
| 5,081,044 A | * | 1/1992 | Buckler et al. ............. | 436/135 |
| 5,696,157 A | * | 12/1997 | Wang et al. ................. | 514/457 |
| 5,851,785 A | * | 12/1998 | Aoyama et al. .............. | 435/28 |

FOREIGN PATENT DOCUMENTS

EP 397 362 11/1990

OTHER PUBLICATIONS

Ichibagase, "Syntheses of Coumarin Derivatives. V. Syntheses of Coumarin–3–carboxylic Acid Derivatives," 50 *Chem. Abstracts* 10715 (1956).

Ichikawa et al., "Syntheses of Coumarin Derivatives. XIV. Preparation of 5–Hydroxy–7–nitro–3–coumarincarboxylic Acid," 59 *Chem. Abstracts* 2757 (1963).

Ichikawa et al., "Studies on the Synthesis of Coumarin Derivatives. XX. Synthesis and Antibacterial Activity of Derivatives of N–substituted 3–Coumarincarboxamide," 16 *Chem. and Pharmaceutical Bull.* 2093 (1968).

Saikachi et al., "Syntheses of Coumarin Derivatives. XV. On the Preparation of Ethyl Pyranobenzoxazole Carboxylates," 16 *Chem. and Pharmaceutical Bull.* 2093 (1966).

Spain, "Biodegradation of Nitroaromatic Compounds," 49 *Ann Rev. of Microbiology* 523 (1955).

Rafii et al., "Reduction of Nitroaromatic Compounds by Anaerobic Bacteria Isolated from the Human Gastrointestinal Tract," 57 *Appl. and Environmental Microbiology* 962 (1991).

Byant et al., "Purification and Characterization of an Oxygen–Insensitive NAD(P)H Nitroreductase from *Enterobacter cloacae*," 266 *J. Biological Chem.* 4119 (1991).

Rieble et al., "Aromatic Nitroreductase From the Basidiomycete *Phanerochaete chrysosporium*," 205 *Biochem. and BioPhys. Res. Comm.* 298 (1994).

* cited by examiner

*Primary Examiner*—Ralph Gitomer
(74) *Attorney, Agent, or Firm*—James C. Lydon (57) ABSTRACT

A nitrocoumarin compound or one of its derivatives which are fluorescent in the reduced state, and the use of these compounds for detecting the presence or absence of at least one microorganism. The invention concerns the use of these compounds, methods for isolating and detecting microorganisms or a group of microorganisms in a sample likely to contain them, and various applications thereof. Also disclosed is a method for detecting nitroaryl reductase activity in a bacteria culture medium.

9 Claims, 4 Drawing Sheets

FLUORESCENT DETECTION METHOD FOR MICROORGANISMS BASED ON NITROCOUMARINS

This application is a continuation of International application PCT/FR99/02704, filed Nov. 5, 1999 and published on May 18, 2000 in the French Language which claims benefit to FRENCH APPLICATION 98/14101 filed Nov. 5, 1998.

This invention concerns a nitro-aromatic compound which can be reduced by microorganisms to produce an amino-aromatic compound.

The invention also relates to the use of a compound in a detection and/or diagnostic test for microorganisms.

The invention further relates to a method for demonstrating the presence of nitroaryl reductase activity in a culture medium containing microorganisms.

Finally, the invention covers a method for the detection of single microorganisms or groups of microorganisms in samples which may contain them.

The article "Syntheses of coumarin derivatives. V Syntheses of coumarin-3-carboxylic acid derivatives" CHEMICAL ABSTRACTS, vol. 50, 1956, page 10715, XP-002109446, describes the synthesis of nitrocoumarin derivatives including the 7-nitrocoumarins. The only application specified is based on their hypnotic and sedative activities. Moreover, their toxicity is dealt with. The article "Syntheses of coumarin derivatives. XIV Preparation of 5-hydroxy-7-nitro-3-coumarincarboxylic acid" CHEMICAL ABSTRACTS, vol. 59, 1963, page 2757, XP-002109447, only describes the synthesis of 5-hydroxy-7-nitrocoumarin carboxylic acid.

The possibility of using these molecules to detect the presence or absence of microorganisms has never been addressed. Therefore, no bacteriological application has ever been contemplated. Moreover, the toxicity results did not encourage those skilled in the art to think about using this type of compound in culture media being used to support the growth of microorganisms.

Certain products synthesized above may have therapeutic applications, in particular those endowed with antibacterial activity. This is documented in the two following articles: the article "Studies on Synthesis of Coumarin Derivatives. XX. Synthesis and Antibacterial Activity of Derivatives of N-Substituted 3-Coumarincarboxamide" CHEMICAL AND PHARMACEUTICAL BULLETIN, vol. 16, no. 11. November 1968 (1968-11) pages 2093–2100, XP-002109448, describes the use of nitrocoumarins as antibacterial agents as does also the article "Synthesis of Coumarin Derivatives. XX. On the Preparation of Ethyl Pyranobenzoxazole carboxylates" CHEMICAL AND PHARMACEUTICAL BULLETIN, vol. 14, 1966, pages 1162–1167, XP-002109449.

However, in our invention, the essential property is that nitrocoumarins—and particularly the 7-nitrocoumarins—fluoresce when they are in the reduced state. This fluorescence depends on whether certain microorganisms are present or not. It should be noted that the toxicity and antibacterial activity of these compounds could only discourage those skilled in the art from contemplating their use in the detection of microorganisms.

The object of this patent application is completely different. It is not in any way associated with detecting a potentially therapeutic activity such as the inhibition of bacterial growth but, in contrast, is a way of detecting microorganisms through an enzyme activity, namely nitroaryl reductase activity which reduces the non-fluorescent 7-nitrocoumarin (or one of its derivatives) into the fluorescent 7-aminocoumarin (or the corresponding derivative). It therefore concerns a fluorescent test for the universal detection of microorganisms in samples which may contain them and in which the inhibition of bacterial growth is not an issue.

Certain bacteria have been known for many years to be able to reduce aromatic nitro-compounds. From E. coli extracts, Asnis (1957) isolated a flavoprotein which could reduce p-nitrobenzoic acid. Since this seminal finding, nitroaryl reductase activities have been described in various types of microorganism, including obligate aerobes such as Pseudomonas spp. (Won et al. 1974) and Nocardia spp. (Villanueva 1964), obligate anaerobes such as Clostridium spp. (Ancermaier & Simon 1983) and Veillonella spp. (McCormick et al. 1976), fungi (Masuda & Ozaki 1993) and eukaryotic parasites (Douch 1975). A whole range of substrates is known as being reducible by bacterial nitroaryl reductases, especially aromatic nitro-compounds such as p-nitrobenzoic acid, p-nitrophenol, p-nitroaniline and 2,4,6-trinitrotoluene (McCormick et al. 1976).

Although a wide range of different substrates is available, none are suitable for the direct detection of nitroaryl reductase through the production of a fluorescent product.

Therefore, this enzyme activity has to be assayed by indirect methods, e.g. by measuring the disappearance of the substrate or some cofactor. Kitamura et al. (1983), investigating the reduction of methyl p-nitrobenzoate and a series of other aromatic nitro-compounds by E. coli extracts, showed that three distinct and well-defined enzyme activities could be chromatographically isolated on a DEAE-cellulose column, and that each of these distinct three fractions required different cofactors for its activity: the first required NADH; the second required NADPH; and the third required both. Enzyme reactivity was assayed by following the change in optical density (OD) at 340 nanometers (nm) due to the consumption of the NADH and/or the NADPH. Consumption of the NADH and/or the NADPH was associated with the formation of two reaction products, namely methyl p-aminobenzoate and methyl p-hydroxylaminobenzoate. Bryant et al. (1981) also studied E. coli nitroaryl reductases, using nitrofurazone as the substrate. In order to assay enzyme activity, they were able to follow changes in OD at 375 nm (the absorption maximum [λ max] of nitrofurazone). Using this method, they detected three distinct activities capable of reducing nitrofurazone. The ability of bacteria to reduce nitrofuranes is of great interest in the field of antibacterial chemotherapy (Peterson et al. 1979, Wentzell & McCalla 1980) and it has been shown that the major E. coli nitroaryl reductase (which is NADPH-dependent) is absent in nitrofurazone-resistant mutants (Bryant et al. 1981).

The object of this invention is a fluorescent substrate based on nitrocoumarin which is suitable for the direct detection of nitroaryl reductase activity. When reduced, this type of aromatic nitro-compound gives a product which is fluorescent and therefore easy to detect. The reaction (I) is shown below:

7-nitrocoumarin derivative

7-aminocoumarin derivative

Unexpectedly, it was found that the vast majority of microorganisms contain nitroreductase activity and are therefore capable of reducing 7-nitrocoumarin derivatives to give a fluorescent product—this is not true of any of the substrates which have been investigated hitherto. Therefore, these derivatives represent a class of universal indicators which make it possible to detect the presence or absence of microorganisms in any given sample.

To this end, this invention concerns a compound for detecting the presence or absence of at least one microorganism. The invention is characterized in that the compound is a nitrocoumarin or one of its derivatives which gives a fluorescent product on reduction.

Particularly, said compound is 7-nitrocoumarin or one of its derivatives.

The compound is characterized by the following structural formula:

in which $R_3$ is either H or COZ, where Z is conducive to the generation of a ketone, an acid or an ester group, or any other aliphatic group, and in which $R_4$ is either H or a trifluoromethyl ($CF_3$) group or any aliphatic group.

According to a modification, $R_3$ consist of $COOCH_3$, $COOC_2H_5$, COOH, $COC_3H_7$, $CONC_4H_4O$ or $COCH_3$ group, and $R_4$ is either H or a $CH_3$ group.

According to another modification, the compound is made up of 7-nitrocoumarin-3-carboxylic acid.

The concentration of 7-nitrocoumarin-3-carboxylic acid ranges from 0.05 to 0.3 mmol/l.

According to a potentially interesting embodiment, the compound described above can be used in a formulation or in combination with one or more other nitrocoumarin compounds or derivatives.

The invention also concerns the use of a compound as defined above in a detection and/or diagnostic test for the presence or absence of microorganisms.

The invention further concerns a first method for detecting single microorganisms or groups of microorganisms in samples which may contain them. This method consists in:

adding to a culture medium containing the sample, at least one nitrocoumarin-based compound, preferably 7-nitrocoumarin or one of its derivatives, and monitoring for the production of a fluorescent product—the presence or absence of a fluorescent signal corresponding to the presence or absence of the suspected microorganism or group of microorganisms.

The invention further concerns a second method for identifying at least one microorganism in a sample which may contain such microorganisms, comprising the following steps:

adding, in a series of wells, a culture medium containing a single carbon source, such as lactose, glucose, sucrose, etc., an aliquot of the test sample and at least one nitrocoumarin-based compound, preferably 7-nitrocoumarin or one of its derivatives, and searching each well for the production of a fluorescent product—the presence or absence of this fluorescence over all of the wells enabling the microorganism to be identified. This second method is also called an assimilation test.

Finally, the invention concerns various applications associated with the detection of microbial growth using at least one compound, as defined above, for:

performing a sterility test, counting the microorganisms present in the sample, testing the susceptibility of a microorganism to an antimicrobial agent, and detecting the presence of at least one microorganism.

The Figures shown are given for reference and explanatory purposes only and are not intended to be in any way limiting. They are designed to make the invention easier to understand.

This invention concerns a series of compounds based on 7-nitrocoumarin which acts as a fluorogenic substrate for the direct detection of nitroaryl reductase activity.

The general structure of nitrocoumarins is illustrated by formula II:

The number of possible substituted derivatives is large so the experiments focused on each of the substitutions and on the various possibilities. The alternatives are listed in Table 1 below. This list mainly concern radicals $R_3$, $R_4$ and $R_8$, which represent the most important substituents.

Nevertheless, groups $R_5$ and $R_6$ are not usually substituted, as it is the case in Table 1. They are made up of hydrogen atoms (H). However, substitution can take place here with the following possibilities:

- at least one of the groups $R_5$ and/or $R_6$ is a $CH_3$ group or another small alkyl group (with fewer than 5 carbon atoms), or
- at least one of the groups $R_5$ and/or $R_6$ is a halide (F, Cl, Br or I), or
- at least one of the groups $R_5$ and/or $R_6$ is a $CH_3O$ group or another small alkoxy group (with fewer than 5 carbon atoms), or
- at least one of the groups $R_5$ and/or $R_6$ is a phenyl (aryl) or an aralkyl group. Whenever only one of the groups $R_5$ or $R_6$ is one of those specified above, there is an H atom at the other position.

Furthermore, it is possible that $R_5$ and $R_6$ participate together in an aromatic ring (a benzenoïd or heterocyclic ring). The structure of this type of molecule is shown opposite.

TABLE 1

Substitutions of the nitrocoumarin core and the resultant compounds

|  | R3 | R4 | R8 |
|---|---|---|---|
| 7-nitrocoumarin | H | H | H |
| 4-methyl-7-nitrocoumarin | H | $CH_3$ | H |
| methyl-7-nitrocoumarin-3-carboxylate | $COOCH_3$ | H | H |
| ethyl-7-nitrocoumarin-3-carboxylate | $COOC_2H_5$ | H | H |
| 7-nitrocoumarin-3-carboxylic acid | COOH | H | H |
| 3-butyryl-7-nitrocoumarin | $COC_3H_7$ | H | H |
| 3-acetyl-4-methyl-7-nitrocoumarin | $COCH_3$ | $CH_3$ | H |
| 7-nitrocoumarin-3-carboxy-morpholide | $CONC_4H_4O$ | H | H |

1°) Materials

A—Culture Medium

The media used were Mueller-Hinton and Trypticase Soy broths and agars obtained from Unipath Ltd, Basingstoke, Great Britain.

B—Substrates and Chemical Reagents

The following substrates were synthesized: 7-nitrocoumarin, 4-methyl-7-nitrocoumarin, methyl-7-nitrocoumarin-3-carboxylate, ethyl-7-nitrocoumarin-3-carboxylate, 7-nitrocoumarin 3-carboxylic acid, 3-butyryl-7-nitrocoumarin, 3-acetyl-4-methyl-7-nitrocoumarin, 7-nitrocoumarin-3-carboxy-morpholide.

C—Apparatus

The following apparatus was used:
- an Anthos 2001 microtiter plate spectrophotometer obtained from Labtech International Limited, Uckfield, Great Britain, and
- a Labtech Biolite F1 microtiter plate fluorescence reader obtained from Labtech International Limited, Uckfield, Great Britain.

D—Nitrocoumarin synthesis

All chemical reagents used in the synthesis of the nitrocoumarins were obtained from the Aldrich Chemical Company Ltd, Gillingham, Great Britain.

The synthetic pathway for 7-nitrocoumarin has been described by LIEBERMANN, M, et al. (1951) Académie des Sciences 232, 2027–2029. It involves heating together under reflux: 12 g nitro-4-salicylic aldehyde, 18 g of anhydrous sodium acetate and 27 g of acetic anhydride. After three hours of refluxing, the reaction mixture is transferred into a mortar and pounded to a paste. Then it is centrifuged and washed, first with small volumes of acetic anhydride and then with water. The resultant material is heated under reflux together with 13 g of $Na_2CO_3$ and 320 $cm^3$ of water. After two hours, the mixture is filtered while still hot and precipitated—still hot—using hydrochloric acid. After cooling, the mixture is centrifuged and the product is recrystallized from 300 $cm^3$ of 50% acetic acid. A second cycle of recrystallization gives a product which melts at 198–200° C.

Synthesis of the various nitrocoumarin derivatives involves the preliminary synthesis of 4-nitrosalicylaldehyde which was performed using a modification of the method described by SEGESSER, J. R., and CALVIN, M. (1942) J. Am. Chem. Soc. 64, 825–826. This involves initial acetylation of 2-methyl-5-nitrophenol followed by two bromine addition steps using N-bromosuccinimide in the presence of benzoyl peroxide as catalyst. This reaction is carried out in carbon tetrachloride as the solvent and yields 2-acetoxy-4-nitrobenzale bromide. The crude dibromide is recrystallized from 1-butanol before conversion to nitrosalicylaldehyde in the following series of reactions.

A mass of 11 g of the pure dibromide is dissolved in 50 ml of anhydrous methanol and the resultant solution is gradually added to 250 ml of a 1% (m/v) solution of sodium in boiling methanol. After refluxing for 45 min, the resultant dark orange solution is allowed to cool before the addition of 100 ml of water. After boiling for a further 15 min, the solution is allowed to cool and its pH is adjusted to 3. The methanol is evaporated off (in a rotary evaporator) and the precipitated 4-nitrosalicylaldehyde is recovered by vacuum filtration. The residue is then recrystallized from dilute ethanol.

Three of the nitrocoumarin derivatives were synthesized using similar methods which are based on Knoevenagel condensation with 4-nitrosalicylaldehyde. Dimethylmalonate (1.45 g, 11 mM) and 4-nitrosalicylaldehyde (1.67 g, 10 mM) are dissolved in 15 ml of ethanol. Then 100 mg of piperidine and 100 μl of cold acetic acid are added and the mixture is refluxed for two hours. The product—methyl-7-nitrocoumarin-3-carboxylate—precipitates out either during the reaction or as the solution cools down. The precipitate is recovered by vacuum filtration and recrystallized from ethanol. For the synthesis of ethyl-7-nitrocoumarin-3-carboxylate and 3-butyryl-7-nitrocoumarin, the dimethyl malonate is replaced with diethyl malonate or ethyl-butyrylacetate respectively.

7-nitrocoumarin-3-carboxylic acid is obtained by refluxing ethyl 7-nitrocoumarin-3-carboxylate (2.63 g, 10 mM) with excess potassium hydroxide solution and aqueous ethanol for one hour. The deep yellow-colored potassium salt is then acidified using hydrochloric acid and, after recovery, the product is washed in a small volume of water and recrystallized from boiling water.

7-nitrocoumarin-3-carboxymorpholide is prepared in the following way. 7-nitrocoumarin-3-carboxylic acid (1.17 g, 5 mM) is dissolved in a mixture of 25 ml of anhydrous tetrahydrofurane and 10 ml of dimethylformamide. This mixture is thoroughly mixed and then 5 mmol of N-methylmorpholine (0.5 g, 5 mM) is added. After cooling to a temperature of below 12° C., isobutyl chloroformate (0.68 g, 5 mM) is added. After 10 min, the morpholide (0.64 g, 7.5 mM) is added. The reaction is allowed to proceed for 30 min at a temperature rigorously maintained at 0° C. Then the mixture is allowed to come to room temperature and left for a further 5 hours. The N-methylmorpholine hydrochloride is removed by filtration and the filtrate transferred into 10 ml of a mixture of ice and water. The solid which precipitates out is then recrystallized in liquid methanol.

Both 4-methyl-7-nitrocoumarin and 3-acetyl-4-methyl-7-nitrocoumarin are synthesized using an alternative procedure based on the oxidation of 7-aminocoumarin. 7-amino-4-methylcoumarin (1.75 g, 10 mM) is resuspended in 10 ml of 75% (m/m) of sulfuric acid and thoroughly mixed. Keeping the temperature below 5° C., a 2.5 ml volume of 7 M sodium nitrite solution is gradually added by means of a long delivery tube pushed down to the bottom of the test tube. The diazonium solution is then mixed for 15 min until the temperature has risen from 2° C. to 5° C. An aliquot of 5 l of ice water containing 2.4 g of sodium tetrafluoroborate is then added to the cold diazonium solution. The ice water at 0° C. is added slowly until a crystalline aggregate of the tetrafluoroborate forms. This precipitate is recovered by vacuum filtration and then washed, first with a small volume of ice water, then with methanol and finally with ether. After rapid air-drying, the yield of the product is 2.2 g.

A mass of 3 g of copper powder and a suspension of cupric oxide (prepared by reducing cupric sulfate with glucose) are added to a cold 4.1 M solution of sodium nitrite. A mass of 2.2 g of the diazonium salt is resuspended in 10 ml of water and the resultant mixture is added stepwise over a period of 20 min, keeping the temperature at between 5 and 15° C. and stirring throughout. The nitrogen is then removed which entails the addition of a small volume of ether in order to prevent foaming. After continuous mixing for 5 hours, the suspension is filtered, washed with water, and then extracted with hot ethyl acetate. The aqueous solution is extracted in the same way. The two extracts are then pooled, washed with water and dried with anhydrous magnesium sulfate. The solvent is evaporated off in a rotary evaporator to yield a yellow residue. Recrystallization of the latter from hot acetic acid gives 0.62 of a lemon yellow-colored product, i.e. 4-methyl-7-nitrocoumarin.

The 3-acetyl-4-methyl-7-nitrocoumarin is prepared using a similar method starting with 3-acetyl-4-methyl-aminocoumarin which is prepared in a similar way to that used for 7-amino-4-methylcoumarin except that ethyl acetoacetate is used instead of ethyl diacetoacetate.

E—Making Up the Substrate Solutions

A sample of the 7-nitrocoumarin derivative is dissolved in 4 ml of hot, distilled water. The mass dissolved to make the stock solution is such that the final concentration of the compound in the assay is 0.105 mmol/l. This solution is added to 96 ml of Mueller-Hinton broth and the mixture is sterile-filtered.

F—Microorganisms Tested

All strains tested were either wild strains or were obtained from international collections (NCTC and ATCC)

2°) Methods and Results

A—Evaluation of the Usefulness of Different Nitrocoumarin Derivatives as Indicators for *Escherichia coli* Growth (NCTC 10418)

1°) Method

A preliminary experiment was conducted using one strain of *Escherichia coli* (NCTC 10418) and the eight nitrocoumarins listed in Table 1, i.e.:

7-nitrocoumarin,
4-methyl-7-nitrocoumarin,
methyl-7-nitrocoumarin-3-carboxylate,
ethyl-7-nitrocoumarin-3-carboxylate,
7-nitrocoumarin 3-carboxylic acid,
3-butyryl-7-nitrocoumarin,
3-acetyl-4-methyl-7-nitrocoumarin, and
7-nitrocoumarin-3-carboxymorpholide.

The *E. coli* was grown for 24 hours at 35° C. on Columbia agar supplemented with sheep blood. The bacteria were then resuspended in sterile, distilled water and heir density was adjusted to 0.5 on the MacFarland scale (i.e. about $10^8$ cells/ml). This suspension was then diluted 100-fold in sterile Mueller-Hinton broth (i.e. to a final density of about $10^6$ cells/ml).

Fifty microliters of each nitrocoumarin solution plus 50 µl of bacterial suspension were then added to the wells of a microtiter plate. The plates were incubated at 35° C. and the optical density and fluorescence of each well was read every 30 min for a total of 4 hours. Optical density (690 nm) readings were made using an Anthos 2001 spectrophotometer (Labtech International Limited), and fluorescence (excitation at 365 nm and emission at 440 nm) readings were made on a Biolite F1 2001 fluorometer (Labtech International Limited).

2°) Results

Figure 1:
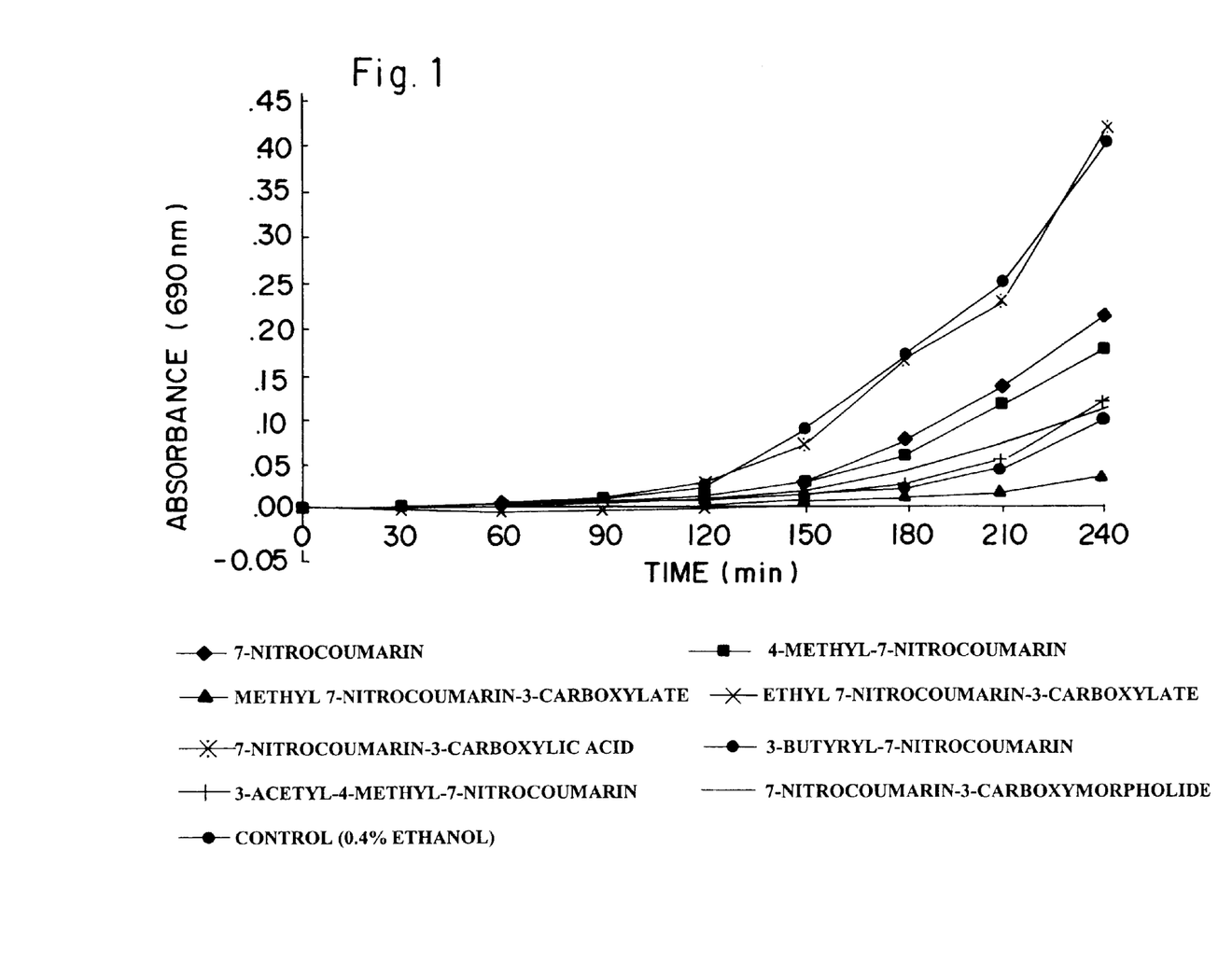
FIG. 1 is a graph showing the effect of a series of different nitrocoumarins (all at a concentration of 0.105 mmol/l) on the growth of E. coli (NCTC 10418) in Mueller-Hinton broth.

FIG. 1 shows the effect of each of the eight nitrocoumarins (at 0.1105 mmol/l) on the growth of *E. coli* (NCTC 10418). It is clear that chemical substitution of the coumarin nucleus has significant effects on the inhibitory activity of the 7-nitrocoumarin. For example, in the presence of 0.105 mmol/l of 7-nitrocoumarin-3-carboxylic acid, no retarded growth is noted. On the other hand, in the presence of the same concentration of methyl-7-nitrocoumarin-3-carboxylate, the OD readings are reduced by a factor of 92% compared with the untreated control. These inhibitory effects correlate with the rate of reduction of the substrate as measured by the generation of a fluorescent signal.

Figure 2:
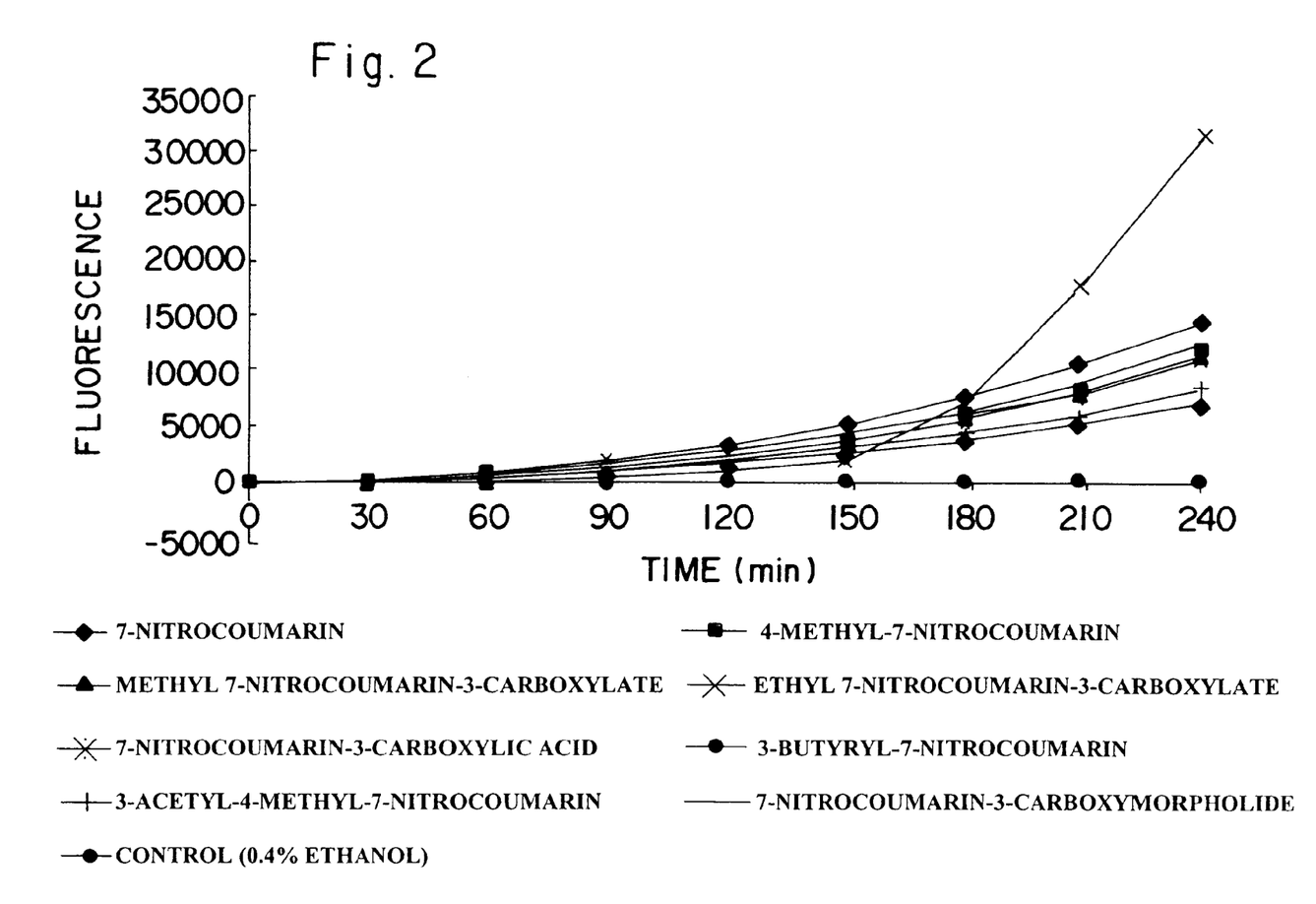
FIG. 2 is a graph showing the fluorescent signal generated by E. coli (NCTC strain 10418) growing in Mueller-Hinton broth in the presence of a series of different nitrocoumarin derivatives (all at a concentration of 0.105 mmol/l).

In FIG. 2, it can be clearly seen that the two most powerful inhibitors—methyl-7-nitrocoumarin-3-carboxylate and 3-butyryl-7-nitrocoumarin—are the least reduced at the end of the four-hour assay. Moreover, 7-nitrocoumarin-3-carboxylic acid (the only compound which does not inhibit *E. coli* growth) is reduced to a far greater extent than any of the other nitrocoumarins with a fluorescent signal which is more than twice as high as that given by any of the other substrates.

In order to make FIGS. 1 and 2 easier to understand, the readings on which they are based are given in the following Tables (Tables 2 and 3).

TABLE 2

Reading corresponding to FIG. 1

| Compound\Time(min) | 0 | 30 | 60 | 90 | 120 | 150 | 180 | 210 | 240 |
|---|---|---|---|---|---|---|---|---|---|
| 7-nitrocoumarin | 0.000 | −0.002 | 0.000 | 0.002 | 0.009 | 0.025 | 0.072 | 0.133 | 0.211 |
| 4-methyl-7-nitrocoumarin | 0.000 | 0.000 | 0.002 | 0.004 | 0.010 | 0.024 | 0.055 | 0.113 | 0.175 |
| methyl-7-nitrocoumarin-3-carboxylate | 0.000 | −0.001 | −0.001 | 0.000 | 0.000 | 0.002 | 0.006 | 0.014 | 0.032 |
| ethyl-7-nitrocoumarin-3-carboxylate | 0.000 | −0.005 | −0.008 | −0.008 | −0.006 | 0.000 | 0.018 | 0.046 | 0.116 |
| 7-nitrocoumarin 3-carboxylic acid | 0.000 | 0.000 | 0.002 | 0.008 | 0.026 | 0.068 | 0.164 | 0.227 | 0.416 |
| 3-butyryl-7-nitrocoumarin | 0.000 | 0.001 | 0.005 | 0.007 | 0.009 | 0.012 | 0.015 | 0.039 | 0.096 |
| 3-acetyl-4-methyl-7-nitrocoumarin | 0.000 | −0.003 | −0.002 | −0.001 | 0.002 | 0.008 | 0.023 | 0.051 | 0.110 |
| 7-nitrocoumarin-3-carboxymorpholide | 0.000 | −0.002 | −0.001 | 0.001 | 0.005 | 0.014 | 0.037 | 0.068 | 0.109 |
| Control | 0.000 | −0.002 | 0.000 | 0.005 | 0.019 | 0.085 | 0.169 | 0.246 | 0.400 |

TABLE 3

Reading corresponding to FIG. 2

| Compound\Time(min) | 0 | 30 | 60 | 90 | 120 | 150 | 180 | 210 | 240 |
|---|---|---|---|---|---|---|---|---|---|
| 7-nitrocoumarin | 0 | 77 | 519 | 1447 | 2915 | 4713 | 7160 | 10182 | 14189 |
| 4-methyl-7-nitrocoumarin | 0 | 15 | 302 | 974 | 2008 | 3299 | 5097 | 7545 | 11125 |
| methyl-7-nitrocoumarin-3-carboxylate | 0 | 174 | 702 | 1297 | 2035 | 2905 | 3946 | 5005 | 6668 |
| ethyl-7-nitrocoumarin-3-carboxylate | 0 | 173 | 814 | 1703 | 2813 | 4126 | 5646 | 7370 | 10859 |
| 7-nitrocoumarin 3-carboxylic acid | 0 | −67 | 4 | 181 | 586 | 1694 | 6724 | 17495 | 31314 |
| 3-butyryl-7-nitrocoumarin | 0 | 64 | 387 | 894 | 1538 | 2344 | 3329 | 4642 | 6845 |
| 3-acetyl-4-methyl-7-nitrocoumarin | 0 | 40 | 390 | 992 | 1804 | 2811 | 4090 | 5576 | 8017 |
| 7-nitrocoumarin-3-carboxymorpholide | 0 | 180 | 665 | 1376 | 2414 | 3796 | 5817 | 8454 | 12263 |
| Control | 0 | −214 | −159 | −205 | −174 | −177 | −131 | −104 | −101 |

B—The Inhibitory Effect of Different Concentrations of 7-nitrocoumarin 3-carboxylic Acid on the Growth of *Escherichia coli* (NCTC Strain 10418)

1°) Method

The effect of the concentration of 7-nitrocoumarin-3-carboxylic acid on the sensitivity of the assay to detect *E. coli* (NCTC strain 10418) was investigated at concentrations of the indicator ranging from 0 to 0.262 mmol/l. All other conditions were identical to those described in section A above.

2°) Results

Figure 3:
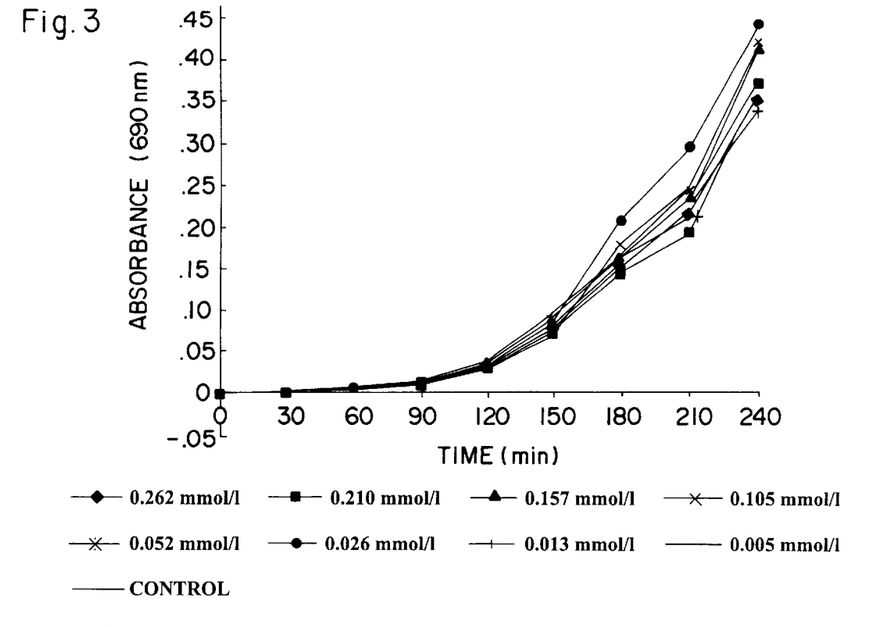
FIG. 3 is a graph showing the growth of E. coli (NCTC strain 10418) in Mueller-Hinton broth in the presence of a series of different concentrations of 7-nitrocoumarin-3-carboxylic acid.

It can be clearly seen from FIG. 3 that the concentration of 7-nitrocoumarin 3-carboxylic acid has no significant effect on *E. coli* growth since the growth curves measured at different concentrations are similar to one another and even similar to that of the control. The fact that this compound has no growth inhibitory activity is reflected by the level of the fluorescent signal resulting from reduction of the nitro groups.

Figure 4:
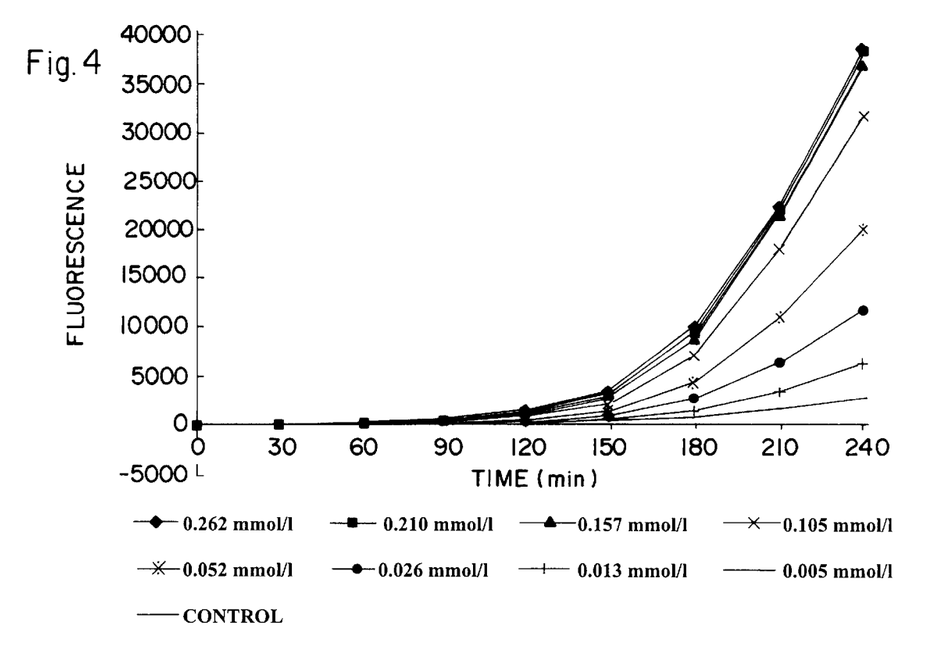
FIG. 4 is a graph showing the fluorescent signal generated by E. coli (NCTC strain 10418) growing in Mueller-Hinton broth in the presence of a series of different concentrations of 7-nitrocoumarin-3-carboxylic acid.

FIG. 4 shows that the fluorescent signal increases with the substrate concentration until saturation at a concentration of about 0.157 mmol/l (36.9 μg/ml). Beyond this point, the sensitivity of the fluorescent reaction is not enhanced.

In order to make FIGS. 3 and 4 easier to read, the readings on which they are based are given in the following Tables (Tables 4 and 5).

TABLE 4

Reading corresponding to FIG. 3

| Compound\Time(min) | 0 | 30 | 60 | 90 | 120 | 150 | 180 | 210 | 240 |
|---|---|---|---|---|---|---|---|---|---|
| 0.262 mmol/l | 0.000 | 0.000 | 0.002 | 0.009 | 0.027 | 0.069 | 0.144 | 0.213 | 0.346 |
| 0.210 mmol/l | 0.000 | 0.000 | 0.003 | 0.010 | 0.027 | 0.072 | 0.138 | 0.187 | 0.346 |
| 0.157 mmol/l | 0.000 | −0.001 | 0.002 | 0.009 | 0.027 | 0.073 | 0.151 | 0.205 | 0.372 |
| 0.105 mmol/l | 0.000 | 0.000 | 0.002 | 0.008 | 0.026 | 0.068 | 0.164 | 0.227 | 0.416 |
| 0.052 mmol/l | 0.000 | 0.001 | 0.003 | 0.011 | 0.031 | 0.082 | 0.153 | 0.225 | 0.408 |
| 0.026 mmol/l | 0.000 | 0.001 | 0.004 | 0.011 | 0.032 | 0.079 | 0.201 | 0.290 | 0.436 |
| 0.013 mmol/l | 0.000 | 0.000 | 0.003 | 0.011 | 0.032 | 0.088 | 0.149 | 0.233 | 0.371 |
| 0.005 mmol/l | 0.000 | 0.000 | 0.003 | 0.011 | 0.034 | 0.090 | 0.155 | 0.246 | 0.411 |
| Control | 0.000 | 0.002 | 0.005 | 0.011 | 0.025 | 0.061 | 0.174 | 0.241 | 0.332 |

TABLE 5

Reading corresponding to FIG. 4

| Compound\Time(min) | 0 | 30 | 60 | 90 | 120 | 150 | 180 | 210 | 240 |
|---|---|---|---|---|---|---|---|---|---|
| 0.262 mmol/l | 0 | 3 | 131 | 446 | 1190 | 3037 | 9721 | 22066 | 37949 |
| 0.210 mmol/l | 0 | −6 | 88 | 354 | 979 | 2588 | 9000 | 21589 | 37823 |
| 0.157 mmol/l | 0 | −74 | 48 | 280 | 811 | 2231 | 8264 | 21022 | 36517 |
| 0.105 mmol/l | 0 | −67 | 4 | 181 | 586 | 1694 | 6724 | 17495 | 31314 |
| 0.052 mmol/l | 0 | −83 | −76 | 33 | 241 | 861 | 4004 | 10584 | 19530 |
| 0.026 mmol/l | 0 | −91 | −110 | −39 | 71 | 467 | 2311 | 6028 | 11387 |
| 0.013 mmol/l | 0 | −113 | −141 | −76 | −22 | 174 | 1068 | 3073 | 5902 |
| 0.005 mmol/l | 0 | −134 | −164 | −122 | −94 | −9 | 406 | 1307 | 2466 |
| Control | 0 | −296 | −159 | −168 | −149 | −156 | −131 | −110 | −119 |

C—The Usefulness of 7-nitrocoumarin 3-carboxylic Acid as an Indicator of the Growth of Various Different Enterobacteriaceae

1°) Method

This experiment was designed to investigate whether or not it would be possible to detect Enterobacteriaceae other than *E. coli* using 7-nitrocoumarin-3-carboxylic acid. The conditions for this experiment were similar to those described for the first experiment (section A).

Five wild strains belonging to the species *Citrobacter diversus*, *Enterobacter agglomerans*, *Hafnia alvei*, *Morganella morganii* and *Shigella sonnei* were tested

2°) Results

Figure 5:
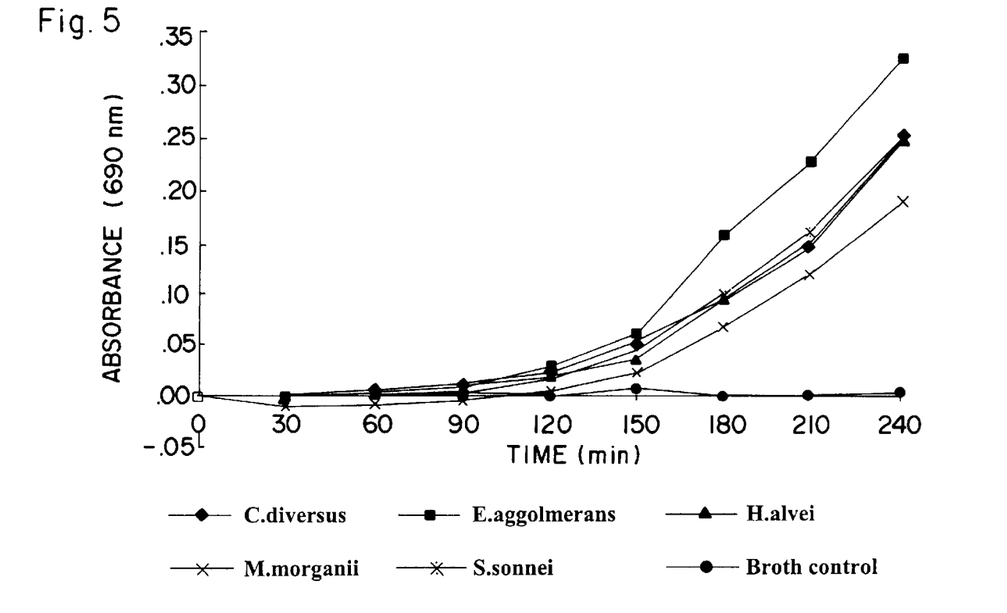
FIG. 5 is a graph showing the growth of a series of wild strains of Enterobacteriaceae species in Mueller-Hinton broth in the presence of 7-nitrocoumarin-3-carboxylic acid at a concentration of 0.17 mmol/l.
Figure 6:
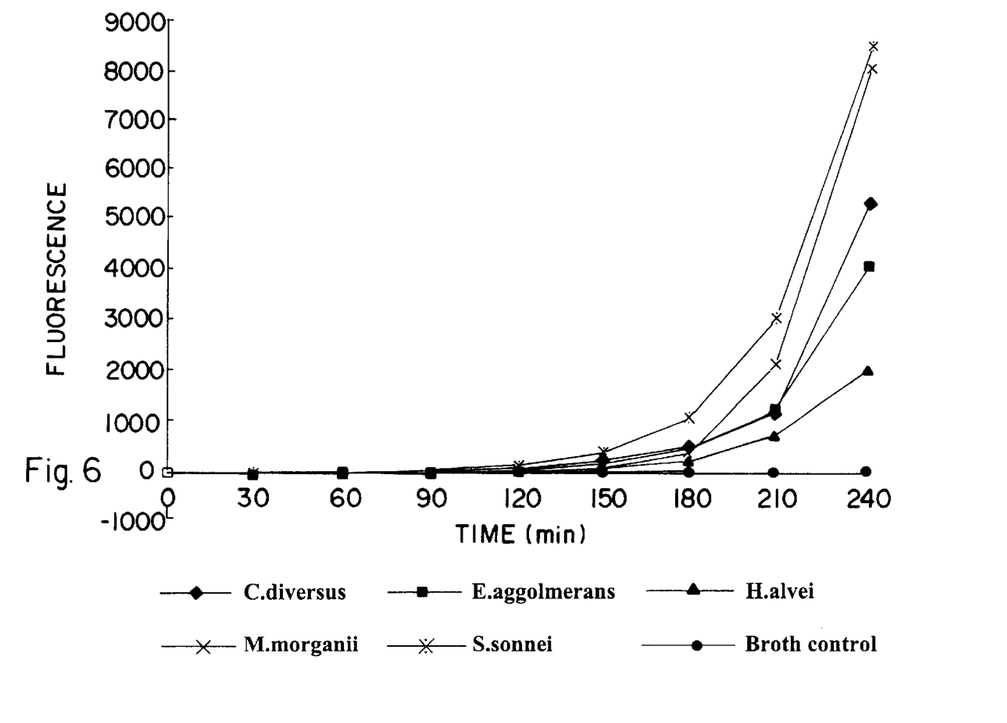
FIG. 6 is a graph showing the reduction of 7-nitrocoumarin-3-carboxylic acid at a concentration of 0.17 mmol/l by the same wild strains of Enterobacteriaceae species as in FIG. 5.

FIG. 6 shows how 7-nitrocoumarin-3-carboxylic acid is reduced by wild strains belonging to five different species of Enterobacteriaceae. All the strains tested were found to be able to reduce this compound. Comparison of the kinetics of fluorescence (FIG. 6) and the growth curves (FIG. 5) reveal close correlation between the fluorescent signal and the rate of growth. This suggests that 7-nitrocoumarin-3-carboxylic acid is a very reliable indicator for growth.

In order to make FIGS. 5 and 6 easier to read, the readings on which they are based are given in the following Tables (Tables 6 and 7).

TABLE 6

Readings corresponding to FIG. 5

| Compound\Time(min) | 0 | 30 | 60 | 90 | 120 | 150 | 180 | 210 | 240 |
|---|---|---|---|---|---|---|---|---|---|
| C. diversus | 0.000 | 0.000 | 0.005 | 0.011 | 0.020 | 0.050 | 0.092 | 0.143 | 0.250 |
| E. agglomerans | 0.000 | −0.002 | 0.002 | 0.006 | 0.027 | 0.057 | 0.155 | 0.225 | 0.323 |
| H. alvei | 0.000 | −0.001 | 0.004 | 0.009 | 0.016 | 0.034 | 0.092 | 0.149 | 0.246 |
| M. morganni | 0.000 | −0.010 | −0.010 | −0.005 | 0.003 | 0.020 | 0.064 | 0.116 | 0.187 |
| S. sonnei | 0.000 | −0.001 | 0.000 | 0.002 | 0.013 | 0.042 | 0.097 | 0.159 | 0.246 |
| Control | 0.000 | −.0002 | −0.002 | 0.003 | −0.002 | 0.005 | −0.003 | −0.001 | 0.003 |

TABLE 7

Readings corresponding to FIG. 6

| Compound\Time(min) | 0 | 30 | 60 | 90 | 120 | 150 | 180 | 210 | 240 |
|---|---|---|---|---|---|---|---|---|---|
| C. diversus | 0 | 3 | 3 | 34 | 92 | 281 | 546 | 1209 | 5393 |
| E. agglomerans | 0 | −15 | −3 | 9 | 74 | 199 | 501 | 1246 | 4099 |
| H. alvei | 0 | −24 | −30 | 0 | 40 | 122 | 260 | 775 | 2048 |
| M. morganii | 0 | −42 | −24 | −15 | 31 | 95 | 403 | 2170 | 8128 |

TABLE 7-continued

Readings corresponding to FIG. 6

| Compound\Time(min) | 0 | 30 | 60 | 90 | 120 | 150 | 180 | 210 | 240 |
|---|---|---|---|---|---|---|---|---|---|
| S. sonnei | 0 | −9 | 15 | 52 | 162 | 434 | 1108 | 3095 | 8567 |
| Control | 0 | 9 | 0 | 24 | 21 | 34 | 43 | 24 | 61 |

Although the results will not be presented here, it has been confirmed that similar kinetic profiles are obtained with most microorganisms, not only the Enterobacteriaceae, but also non-fermenting Gram-positive bacilli, Staphylococcus spp., Streptococcus spp., Listeria spp. and yeasts. All were capable of reducing nitrocoumarin derivatives (in particular 7-nitrocoumarin-3-carboxylic acid) to give a fluorescent signal. This shows the broad applicability of this method of detecting growth, as illustrated by the results of the following series of experiments.

D—The Usefulness of 7-nitrocoumarin-3-carboxylic Acid as a Growth Indicator for a Wide Variety of Different Types of Microorganism 1°) Method This experiment was performed to test 7-nitrocoumarin-3-carboxylic acid on sixteen (16) different types of microorganism, including one yeast species. A list of all the species tested is given in Table 8 below.

A mass of 10 mg of the indicator was dissolved in 4 ml of hot, distilled water and this solution was then added to 96 ml of Trypticase Soy broth. The resultant mixture was sterile-filtered.

All the microorganisms were grown for 24 hours in Trypticase Soy broth at 35° C. Each culture was then diluted 1,000-fold in Trypticase Soy broth and then serial 10-fold dilutions were made in more Trypticase Soy broth until the test aliquot contained no more microbial cells.

The resultant dilutions ranged from $10^{-3}$ to $10^{-13}$.

Fifty microliters of each dilution plus 50 $\mu$l of Trypticase Soy broth were added to wells of a microtiter plate with or without 7-nitrocoumarin-3-carboxylic acid.

The plates were read (T zero) and then incubated at 35° C. before being read again after 24 hours. Two different readings were made at each time point:
- of the optical density (690 nm), using an Anthos 2001 spectrophotometer (Labtech International Limited) for wells without any 7-nitrocoumarin-3-carboxylic acid, and
- of the fluorescence (excitation at 365 nm and emission at 440 nm), using a Biolite F1 2001 fluorometer (Labtech International Limited), for wells containing 7-nitrocoumarin-3-carboxylic acid.

In order to check the correlation between growth and the fluorescence results, the contents of each well were seeded on Columbia agar supplemented with sheep blood.

2°) Results 7-nitrocoumarin-3-carboxylic acid was tested against sixteen different microorganisms which represented a broad variety of different bacterial species plus one yeast, as shown in Table 8 below.

Fluorescence readings (the first line for each strain) and optical density readings (the second line for each strain) obtained after 24 hours of culture are shown in Table 8. In order to check the correlation between growth and the fluorescence results, and to confirm that the indicator was non-toxic, the contents of each well were seeded on Columbia agar supplemented with sheep blood. The data points corresponding to wells which grew out colonies are shown in italics in the Table.

The results shown in the Table demonstrate that the fluorescence readings (due to reduction of the indicator) correlate closely with microbial growth patterns for all the species tested. The odd minor differences observed can be explained by small variations in the number of viable cells in the microtiter plate wells, especially when it comes to the limiting dilutions where the inoculum might contain only one single microorganism. Therefore, a fluorescence-based test can be used instead of a growth assay. Using 7-nitrocoumarin-3-carboxylic acid as a fluorescent indicator of growth would seem to make for a very sensitive test which is capable of detecting very small numbers of microorganisms; it can be judged that, when limiting dilution methods such as those adopted in this experiment are practiced, this assay is capable of detecting a single viable cell.

It should be noted that the yeast species tested here (Candida albicans) gave only a faint fluorescent signal in comparison to that given by the bacteria. This is due to the use of Trypticase Soy broth which is not an ideal medium for the propagation of yeast. Although the results are not presented here, if a medium which is more suitable for yeast such as RPMI is used, the fluorescent signal is comparable to that generated by the bacteria.

The results are presented in Table 8 below. Because the number of dilutions is so high (eleven dilutions from $10^{-3}$ to $10^{-13}$ plus a twelfth "blank" reading used as the control) and in order to make the results easier to assess, the Table has been divided into two sections: the first section covers the dilutions between $10^{-3}$ and $10^{-9}$; and the second covers the dilutions between $10^{-10}$ and $10^{-13}$ and the control.

After 24 hours in the presence of 7-nitrocoumarin-3-carboxylic acid: fluorescence readings (line 1) and optical density readings (line 2) for serial dilutions of suspensions of a variety of different microorganisms.

| Dilution factor for suspension | $10^{-3}$ | $10^{-4}$ | $10^{-5}$ | $10^{-6}$ | $10^{-7}$ | $10^{-8}$ | $10^{-9}$ |
|---|---|---|---|---|---|---|---|
| Acinetobacter baumanii (ATCC 19606) | 27016 | 11695 | 12525 | 8912 | 6953 | 1651 | 1705 |
| Acinetobacter baumanii (ATCC 19606) | 0.447 | 0.307 | 0.240 | 0.085 | 0.071 | 0.017 | 0.002 |

-continued

After 24 hours in the presence of 7-nitrocoumarin-3-carboxylic acid:
fluorescence readings (line 1) and optical density readings (line 2) for serial dilutions of
suspensions of a variety of different microorganisms.

| | | | | | | | |
|---|---|---|---|---|---|---|---|
| *Acinetobacter calcoaceticus* (ATCC 7844) | 29657 | 18288 | 12311 | 12223 | 11635 | 14858 | 13353 |
| *Acinetobacter calcoaceticus* (ATCC 7844) | 0.522 | 0.714 | 0.669 | 0.565 | 0.290 | 0.404 | 0.208 |
| *Acinetobacter haemolyticus* (ATCC 17906) | 19231 | 17403 | 12614 | 9727 | 4236 | 1981 | 1938 |
| *Acinetobacter haemolyticus* (ATCC 17906) | 0.063 | 0.055 | 0.061 | 0.047 | 0.016 | −0.003 | −0.001 |
| *Brevundimonas vesicularis* (ATCC 11426) | 2543 | 1962 | 1861 | 1941 | 1928 | 1889 | 1929 |
| *Brevundimonas vesicularis* (ATCC 11426) | 0.112 | 0.037 | 0.006 | −0.012 | −0.001 | 0.005 | −0.002 |
| *Burkholderia cepacia* (ATCC 25416) | 16978 | 16719 | 16808 | 15800 | 11973 | 1969 | 1996 |
| *Burkholderia cepacia* (ATCC 25416) | 0.594 | 0.637 | 0.536 | 0.602 | 0.571 | −0.001 | 0.000 |
| *Listeria ivanovii* (wild strain) | 16246 | 44910 | 13185 | 44865 | 9251 | 8137 | 44425 |
| *Listeria ivanovii* (wild strain) | 0.312 | 0.269 | 0.384 | 0.295 | 0.298 | 0.178 | 0.001 |
| *Moraxella nonliquefaciens* (ATCC 19975) | 28160 | 27889 | 28439 | 27648 | 27385 | 27196 | 1974 |
| *Moraxella nonliquefaciens* (ATCC 19975) | 0.828 | 0.693 | 0.666 | 0.693 | 0.708 | 0.697 | 0.000 |
| *Moraxella osloensis* (ATCC 19976) | 11426 | 9949 | 7700 | 5875 | 1925 | 1941 | 1977 |
| *Moraxella osloensis* (ATCC 19976) | 0.056 | 0.044 | 0.051 | 0.059 | 0.000 | 0.001 | 0.000 |
| *Pseudomonas fluorescens* (ATCC 13525) | 8985 | 1774 | 1657 | 1625 | 1716 | 1690 | 1736 |
| *Pseudomonas fluorescens* (ATCC 13525) | 0.005 | −0.002 | −0.002 | −0.004 | −0.001 | −0.003 | −0.002 |
| *Pseudomonas putida* (ATCC 12633) | 12589 | 9810 | 7670 | 6806 | 5714 | 1715 | 1664 |
| *Pseudomonas putida* (ATCC 12633) | 0.567 | 0.483 | 0.431 | 0.465 | 0.483 | −0.002 | 0.000 |
| Dilution factor for suspension | $10^{-3}$ | $10^{-4}$ | $10^{-5}$ | $10^{-6}$ | $10^{-7}$ | $10^{-8}$ | $10^{-9}$ |
| *Serratia marcescens* (NCTC 10211) | 47178 | 49470 | 45804 | 45454 | 45637 | 43088 | 48320 |
| *Serratia marcescens* (NCTC 10211) | 0.543 | 1.001 | 0.464 | 0.487 | 1.240 | 0.549 | 1.051 |
| *Shewanella putrefaciens* (ATCC 8071) | 40277 | 37262 | 34890 | 32034 | 31793 | 1911 | 1902 |
| *Shewanella putrefaciens* (ATCC 8071) | 0.364 | 0.267 | 0.139 | 0.106 | 0.108 | −0.003 | −0.001 |
| *Shigella sonnei* (NCTC 8586) | 51755 | 50254 | 50166 | 50278 | 49882 | 47370 | 1816 |
| *Shigella sonnei* (NCTC 8586) | 0.183 | 0.209 | 0.207 | 0.269 | 0.215 | 0.050 | 0.000 |
| *Staphylococcus aureus* (NCTC 6571) | 46607 | 45207 | 44544 | 43559 | 41437 | 1678 | 1666 |
| *Staphylococcus aureus* (NCTC 6571) | 0.507 | 0.484 | 0.497 | 0.507 | 0.444 | −0.003 | −0.001 |
| *Streptococcus mitis* (NCTC 12261) | 20988 | 21541 | 19899 | 19619 | 17228 | 1682 | 1676 |
| *Streptococcus mitis* (NCTC 12261) | 0.209 | 0367 | 0.325 | 0.300 | 0.257 | −0.002 | 0.000 |
| *Candida albicans* (ATCC 90028) | 2847 | 2609 | 2335 | 2041 | 1693 | 1745 | 1693 |
| *Candida albicans* (ATCC 90028) | 0.49 | 0.419 | 0.308 | 0.403 | −0.003 | 0.001 | 0.000 |
| Control with no microorganism | 1785 | 1727 | 1779 | 1755 | 1786 | 1724 | 1712 |
| Control with no microorganism | 0.003 | 0.001 | 0.000 | −0.003 | −0.005 | −0.002 | −0.001 |

| | | | | | |
|---|---|---|---|---|---|
| Dilution factor for suspension | $10^{-10}$ | $10^{-11}$ | $10^{-12}$ | $10^{-13}$ | "blank" |
| *Acinetobacter baumanii* (ATCC 19606) | 1718 | 1678 | 1687 | 1660 | 1671 |
| *Acinetobacter baumanii* (ATCC 19606) | −0.001 | 0.000 | −0.001 | 0.002 | 0.000 |
| *Acinetobacter calcoaceticus* (ATCC 7844) | 10862 | 1712 | 1654 | 1699 | 1704 |
| *Acinetobacter calcoaceticus* (ATCC 7844) | 0.200 | −0.001 | −0.001 | −0.001 | 0.000 |
| *Acinetobacter haemolyticus* (ATCC 17906) | 2005 | 1947 | 1904 | 1938 | 1907 |
| *Acinetobacter haemolyticus* (ATCC 17906) | −0.002 | 0.000 | −0.001 | −0.002 | −0.001 |
| *Brevundimonas vesicularis* (ATCC 11426) | 1910 | 1938 | 1919 | 1877 | 1840 |
| *Brevundimonas vesicularis* (ATCC 11426) | 0.000 | −0.001 | −0.001 | −0.003 | 0.006 |
| *Burkholderia cepacia* (ATCC 25416) | 1950 | 1925 | 1965 | 1914 | 1874 |
| *Burkholderia cepacia* (ATCC 25416) | −0.002 | 0.002 | −0.002 | −0.002 | −0.001 |
| *Listeria ivanovii* (wild strain) | 1663 | 1651 | 1691 | 1682 | 1680 |
| *Listeria ivanovii* (wild strain) | −0.001 | 0.000 | 0.000 | 0.000 | −0.001 |
| *Moraxella nonliquefaciens* (ATCC 19975) | 2057 | 2002 | 1956 | 1907 | 1969 |
| *Moraxella nonliquefaciens* (ATCC 19975) | −0.002 | 0.000 | −0.001 | 0.001 | 0.000 |
| *Moraxella osloensis* (ATCC 19976) | 2039 | 1938 | 1907 | 1945 | 1880 |
| *Moraxella osloensis* (ATCC 19976) | 0.001 | 0.000 | 0.000 | 0.000 | 0.000 |
| *Pseudomonas fluorescens* (ATCC 13525) | 1666 | 1691 | 1666 | 1624 | 1596 |
| *Pseudomonas fluorescens* (ATCC 13525) | −0.004 | −0.002 | 0.000 | −0.002 | 0.000 |
| *Pseudomonas putida* (ATCC 12633) | 1660 | 1651 | 1660 | 1657 | 1648 |
| *Pseudomonas putida* (ATCC 12633) | −0.002 | 0.001 | 0.001 | 0.001 | 0.001 |
| *Serratia marcescens* (NCTC 10211) | 1678 | 1641 | 1636 | 1621 | 1630 |
| *Serratia marcescens* (NCTC 10211) | −0.002 | −0.001 | 0.001 | −0.001 | −0.001 |
| *Shewanella putrefaciens* (ATCC 8071) | 1972 | 1917 | 1935 | 1990 | 1905 |

| | | | | | |
|---|---|---|---|---|---|
| Dilution factor for suspension | $10^{-10}$ | $10^{-11}$ | $10^{-12}$ | $10^{-13}$ | "blank" |
| *Shewanella putrefaciens* (ATCC 8071) | −0.002 | 0.001 | −0.001 | −0.002 | 0.000 |
| *Shigella sonnei* (NCTC 8586) | 1990 | 1960 | 1956 | 1911 | 1778 |
| *Shigella sonnei* (NCTC 8586) | −0.003 | 0.003 | −0.001 | −0.004 | 0.000 |
| *Staphylococcus aureus* (NCTC 6571) | 1666 | 1620 | 1706 | 1669 | 1746 |
| *Staphylococcus aureus* (NCTC 6571) | −0.001 | 0.001 | 0.003 | 0.000 | 0.000 |
| *Streptococcus mitis* (NCTC 12261) | 1691 | 1636 | 1644 | 1669 | 1682 |
| *Streptococcus mitis* (NCTC 12261) | −0.002 | 0.001 | −0.003 | −0.003 | −0.003 |
| *Candida albicans* (ATCC 90028) | 1751 | 1666 | 1702 | 1666 | 1672 |
| *Candida albicans* (ATCC 90028) | −0.005 | −0.002 | 0.005 | 0.000 | 0.000 |

| After 24 hours in the presence of 7-nitrocoumarin-3-carboxylic acid: fluorescence readings (line 1) and optical density readings (line 2) for serial dilutions of suspensions of a variety of different microorganisms. | | | | | |
|---|---|---|---|---|---|
| Control with no microorganism | 1730 | 1734 | 1700 | 1639 | 1734 |
| Control with no microorganism | −0.001 | −0.001 | 0.001 | −0.001 | −0.001 |

3°) Conclusions

Derivatives of 7-nitrocoumarin, notably 7-nitrocoumarin-3-carboxylic acid, constitute a family of universal fluorescent indicators for the growth of microorganisms.

These novel indicators have numerous applications in microbiology and are relevant to all methods based on the detection of microbial growth. Among the possible applications, the following could be singled out:

- microorganism sensitivity to antibiotic and antifungal testing methods,
- identification methods based on assimilation tests (detection of growth in the presence of substrates which can be used as the sole carbon source),
- sterility testing on a sample (to confirm the absence of any microorganisms),
- any test to detect microorganisms in samples which may contain them, be they clinical, industrial (e.g. in the food processing, pharmaceutical and cosmetics industries) or environmental samples, and
- any kind of counting of microorganisms in a sample, in particular counts based on determining the most probable number, as are routinely practiced in the food processing industry.

We claim:

1. A method for detecting a single microorganism or a group of microorganisms in a sample, comprising:
   adding a non-fluorescent compound to a culture medium which contains the sample, wherein said non-fluorescent compound is 7-nitrocoumarin or a non-fluorescent derivative thereof,
   reducing said non-fluorescent compound to a fluorescent compound by reaction with at least one microorganism contained in said sample,
   detecting a fluorescent signal corresponding to said microorganism or group of microorganisms from said sample.

2. The method of claim 1, wherein said non-fluorescent compound conforms to the following general formula:

wherein
   $R_3$ is either H or COZ, where Z is conducive to the generation of a ketone, an acid or an ester group, or any other aliphatic group, and
   $R_4$ is either H or a trifluoromethyl ($CF_3$) group or any aliphatic group;
   $R_5$ is H, a halide atom, a $C_{1-4}$ alkyl group, a $C_{1-4}$ alkoxy group, a phenyl group or an alkaryl group;
   $R_6$ is H, a halide atom, a $C_{1-4}$ alkyl group, a $C_{1-4}$ alkoxy group, a phenyl group or an alkaryl group; or $R_5$ and $R_6$ can together form an aromatic ring; and
   $R_8$ is H.

3. The method of claim 2, wherein $R_3$ is a member selected from the group consisting of $COOCH_3$, $COOC_2H_5$, COOH, $COC_3H_7$, $CONC_4H_4O$ and $COCH_3$, and $R_4$ is H or a $CH_3$ group.

4. The method of claim 2, wherein said compound is 7-nitrocoumarin-3-carboxylic acid.

5. The method of claim 4, wherein a concentration of said 7-nitrocoumarin-3-carboxylic acid is between 0.05 and 0.3 mmol/l.

6. The method of claim 1, further comprising the steps of:
   measuring the fluorescent signal; and
   determining whether there has been microbial growth to check the sterility of said sample, or alternatively, the presence of at least one microorganism.

7. The method of claim 1, further comprising the steps of:
   measuring the fluorescent signal;
   determining whether there has been microbial growth; and
   counting the number of microorganisms present in the sample.

8. The method of claim 1, further comprising the steps of:
   measuring the fluorescent signal;
   adding an antimicrobial agent to said sample; and
   determining whether there has been microbial growth to determine the susceptibility of a microorganism to an antimicrobial agent.

9. A method for identifying at least one microorganism in a sample which may contain such a microorganism, comprising:
   adding a non-fluorescent compound selected from the group consisting of 7-nitrocoumarin or a derivative thereof to a plurality of individual identification wells, each well containing a culture medium based on a single carbon source and an aliquot of a test sample,
   illuminating each of said identification wells with light at an excitation wavelength,
   monitoring said plurality of identification wells for emission of a fluorescent signal, the presence or absence of a fluorescent signal from each of said identification wells making it possible to identify a microorganism in said sample.

* * * * *

UNITED STATES PATENT AND TRADEMARK OFFICE
CERTIFICATE OF CORRECTION

PATENT NO.    : 6,555,332 B2
DATED         : April 29, 2003
INVENTOR(S)   : Arthur James and Daniel Monget It is certified that error appears in the above-identified patent and that said Letters Patent is hereby corrected as shown below:

Column 18,
Lines 47-64, please rewrite Claim 9 to read as follows:
9. A method for identifying at least one microorganism in a sample which may contain such a microorganism, comprising:
    adding a non-fluorescent compound selected from the group consisting of 7-nitrocoumarin or a derivative thereof to a plurality of individual identification wells, each well containing a culture medium based on a single carbon source and an aliquot of the sample,
    illuminating each of said indentification wells with light at an excitation wavelength,
    monitoring said plurality of identification wells for emission of a fluorescent signal,
    correlating the presence or absence of a fluorescent signal from each of said identification wells to identify a microorganism in said sample.

Signed and Sealed this

Second Day of September, 2003

JAMES E. ROGAN
*Director of the United States Patent and Trademark Office*